United States Patent [19]
Vito

[11] Patent Number: 5,931,838
[45] Date of Patent: Aug. 3, 1999

[54] FIXATION ASSEMBLY FOR ORTHOPEDIC APPLICATIONS

[76] Inventor: Raymond P. Vito, 2224 Riada Dr., NW., Atlanta, Ga. 30305

[21] Appl. No.: 09/014,494

[22] Filed: Jan. 28, 1998

Related U.S. Application Data

[60] Provisional application No. 60/036,469, Jan. 28, 1997.
[51] Int. Cl.$^6$ .................................................. A61B 17/56
[52] U.S. Cl. .................. 606/61; 606/73; 606/62; 606/63; 606/71; 606/69; 606/70; 606/60
[58] Field of Search ................................ 606/61, 73, 63, 606/62, 70, 69, 71, 60; 411/172, 190, 352, 353, 512, 516, 517

[56] References Cited

U.S. PATENT DOCUMENTS

| | | | |
|---|---|---|---|
| 2,922,456 | 1/1960 | Kann | 411/353 |
| 3,414,154 | 12/1968 | Rose et al. | 411/353 |
| 3,762,455 | 10/1973 | Anderson, Jr. | 411/190 |
| 3,894,467 | 7/1975 | Brescia | 411/352 |
| 5,269,784 | 12/1993 | Mast | 606/73 |
| 5,398,664 | 3/1995 | Betz | 411/517 |
| 5,639,113 | 6/1997 | Goss et al. | 411/353 |

*Primary Examiner*—Michael Buiz
*Assistant Examiner*—(Jackie) Tan-Uyen Thi Ho
*Attorney, Agent, or Firm*—Jones & Askew, LLP

[57] ABSTRACT

An improved fixation assembly for orthopedic applications. The fixation assembly includes a screw having an upper shank portion, a middle section with a recessed area, and a lower threaded section. A locking ring surrounds the recessed area of the screw, with the diameter of the locking ring being greater than the diameter of the recessed area of said screw and less than the diameter of the shank and threaded sections of the screw. The screw and locking ring combination is used to attach an orthopedic plate to a bone. The orthopedic plate includes a hole for receiving the screw and the locking ring. The hole includes an upper section and a lower section, wherein the width of the upper section is less than the width of the locking ring so that the locking ring is compressed while in the upper section of the hole. The width of the lower section is greater than the width of the locking ring so that the locking ring is not compressed while in the lower section of the hole.

13 Claims, 2 Drawing Sheets

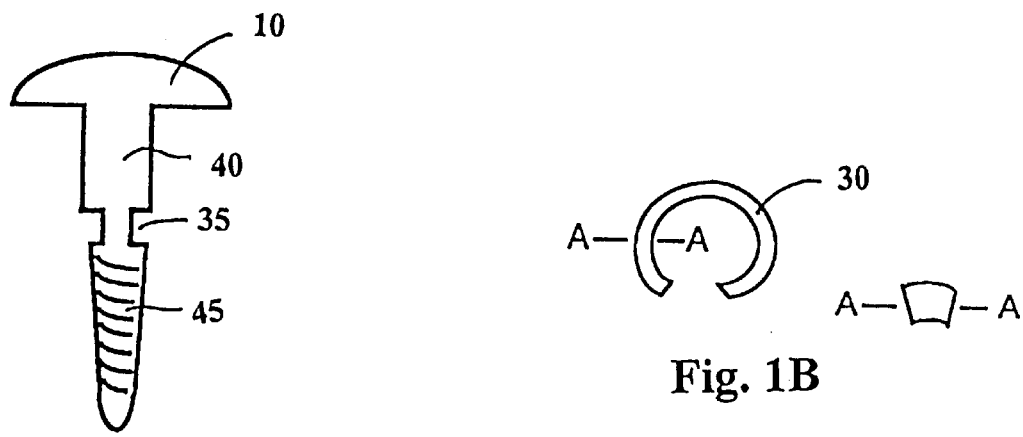
Fig. 1A
Fig. 1B
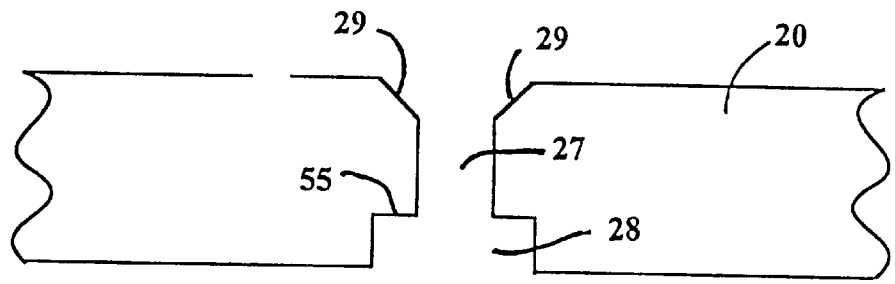
Fig. 1C
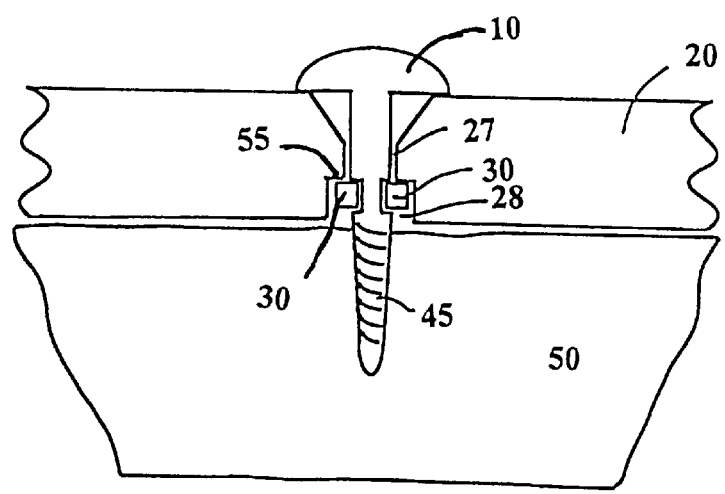
Fig. 1D

FIXATION ASSEMBLY FOR ORTHOPEDIC APPLICATIONS

REFERENCE TO PRIOR APPLICATION

This application claims the benefit of U.S. Provisional Application Ser. No. 60/036,469, filed Jan. 28, 1997.

TECHNICAL FIELD

This invention relates generally to orthopedic fixation assemblies, and in particular to an improved fixation assembly for attaching an orthopedic plate to a bone with one or more screws.

BACKGROUND OF THE INVENTION

Orthopedic fixation assemblies of various types are routinely used in orthopedic applications such as fracture fixation and spinal fusion. These fixation assemblies usually consist of an orthopedic plate that is attached to the adjacent bone by one or more screws. Both orthopedic plates and screws are available in a number of shapes and materials.

One of the major problems associated with using conventional orthopedic fixation assemblies is screw loosening and subsequent screw migration. These can have catastrophic consequences in the case of cervical spine fixation where a loose screw can penetrate the esophagus causing infection and spinal cord damage. Another problem with existing orthopedic fixation assemblies is that the load distribution among the screws tends to be uneven, resulting in less desirable fixation between the plate and the bone.

Therefore, there is a need for an improved fixation assembly for orthopedic applications that reduces the likelihood of screw loosening and screw migration.

There is also a need for an improved fixation assembly for orthopedic applications that improves the fixation between the orthopedic plate and the adjacent bone by providing a more even load distribution among the screws.

SUMMARY OF THE INVENTION

As will be seen, the present invention satisfies the foregoing needs. Briefly described, the present invention provides an improved orthopedic fixation assembly that prevents the screws from loosening and migrating out of the bone by using a screw and plate combination for which the screw, once threaded into the bone, becomes rigidly fixed to the orthopedic plate. Another important consequence of the rigid connection between the screw and the plate is to better distribute the load among the screws, resulting in improved fixation to the bone.

More particularly described, the fixation assembly of the present invention includes an improved orthopedic plate that is secured to the bone by one or more specially designed screws. The screws are designed with a recessed area just below the shank of the screw and above the threaded portion. This recessed area serves to hold an elastic locking ring, e.g., a split ring or a crown ring.

The orthopedic plate includes a hole for receiving the screw and locking ring combination. The hole in the plate has two distinct regions, a narrow upper region and a wider lower region. Specifically, the width of the upper region is less than the width of the locking ring, while the width of the lower region is greater than the width of the locking ring. When the orthopedic plate is attached to the bone, the plate is oriented so that the wider lower region of the plate hole is adjacent to the bone and the narrow upper region is away from the bone.

Due to the relative size of the parts, the locking ring must elastically compress through the narrow upper region of the plate hole while the screw is threaded into the bone. The compression of the locking ring is made possible by the recessed area in the screw. Thus the locking ring compresses into the recessed area as it passes through the narrow upper region of the plate hole. As the screw is advanced further into the bone, the locking ring advances to the wider lower region of the plate hole, where the locking ring can again expand to its original size.

In this position, the screw cannot loosen or migrate out of the bone as translation of the screw is impeded by the interference between the locking ring and a shoulder in the lower region of the plate hole. Nonetheless, the screw is free to rotate, should additional tightening be needed to more firmly secure the plate to the bone.

BRIEF DESCRIPTION OF THE DRAWINGS

FIG. 1A is a side view illustration of the screw constructed and operative in accordance with the embodiments of the present invention.

FIG. 1B is view and cross sectional view illustration of the, locking ring constructed and operative in accordance with the preferred embodiment of the present invention.

FIG. 1C is a side view illustration of the orthopedic plate constructed and operative in accordance with the embodiments of the present invention.

FIG. 1D is a side view illustration of the assembled fixation assembly constructed and operative in accordance with the preferred embodiment of the present invention.

DETAILED DESCRIPTION

Figure 2A:
FIG. 2A is a view illustration of the locking ring constructed and operative in accordance with an alternative embodiment of the present invention.

Referring now to the drawing figures, in which like numerals indicate like elements or steps throughout the several views, the preferred embodiment of the present invention will be described. In general, the present invention provides an improved fixation assembly for orthopedic applications. The fixation assembly consists of the combination of an improved orthopedic plate that is attached to a bone by one or more specially designed screws. The screw includes an upper shank portion, a lower threaded portion and a recessed area in the middle. The recessed area serves to hold an elastic locking ring such as a split ring or a crown ring.

The orthopedic plate includes a hole for receiving the screw and locking ring combination. The upper region of each hole is relatively narrow, while the lower region of each hole is relatively wide. A shoulder is formed at the junction of the upper and lower regions.

As the screw is threaded through the hole in the plate and into the bone, the elastic locking ring compresses into the recessed area of the screw as it passes through the narrow upper portion of the plate and then expands to its original size when it reaches the wider lower region of the plate. In this position, the locking ring locks the plate into place on the bone by preventing the screw from unintentionally loosening and migrating out of the bone. Nonetheless, the screw is free to rotate should additional tightening be needed to more firmly secure the plate to the bone.

Referring to FIGS. 1A–1D, the preferred embodiment of the present invention is shown. The fixation assembly consists of the combination of a screw 10, an orthopedic plate 20 and an elastic locking ring 30. The configuration of the screw 10 is shown in FIG. 1A. The screw 10 includes an upper shank portion 40, a lower threaded portion 45 and a middle portion with a recessed area 35. The screw 10 is preferably made of titanium or stainless steel with a porous coating to promote bone growth.

The recessed area 35 of the screw 10 serves to hold an elastic locking ring 30. In the preferred embodiment, locking ring 30 is a split ring, as shown in FIG. 1B. Locking ring 30 is preferably made from an elastic material such as titanium, stainless steel, polymer or a shape memory alloy, but any other suitable material that is capable of being elastically deformed may be used. The locking ring 30 and the recessed area 35 of the screw 10 are of such dimensions that the locking ring 30 must be elastically deformed in order for it to slide into the recessed area 35. Thus, the inside diameter of the locking ring 30 in its normal or equilibrium state is less than the diameter of the shank 40 and threaded portion 45 of the screw, but is greater than the diameter of the recessed area 35. Once in the recessed area 35, the locking ring 30 is free to move but translation beyond the recessed area 35 is impeded by the interference between the locking ring 30 and the upper and lower shoulders of the recessed area 35.

With the locking ring 30 held in the recessed area 35 of the screw 10, the screw can be used to attach an orthopedic plate to a bone. The orthopedic plate, shown in FIG. 1C, is preferably made of titanium, stainless steel or polymer, but other materials may also be used. Plate 20 includes a hole 25 for receiving the screw and locking ring combination. The hole includes two distinct regions, an upper region 27 and a lower region 28. A shoulder 55 is formed at the junction between the upper region 27 and the lower region 28.

The upper region 27 of the plate hole 25 is relatively narrow, while the lower region 28 is relatively wide. More particularly, the width of the narrow upper region 27 is less than the width of the locking ring 30 (FIG. 1B), while the width of the wide lower region 28 is greater than the width of the locking ring 30.

In application, the orthopedic plate may be attached to a bone with the screw and locking ring combination, as shown in FIG. 1D. To attach the plate 20 to the bone 50, the screw 10 and locking ring 30 combination is inserted into the plate hole 25 and threaded into the bone. The plate 20 is arranged so that the wider lower region 28 of the plate hole 25 is adjacent to the bone 50, while the narrow upper region 27 is away from the bone.

It will be appreciated that due to the relative size of the locking ring 30 and the narrow upper region 27 of the plate hole 25, the locking ring 30 must be compressed into the recessed area 35 of the screw 10 as the screw is threaded into the bone 50. The top edges 29 of the plate hole 25 may be tapered to facilitate compression of the locking ring 30 and passage of the screw 10.

As the screw 10 is threaded further into the bone 50, the locking ring 30 passes through the narrow upper region 27 of the plate hole 25 and into the wider lower region 28. Because the width of the wider lower region 28 is greater than the width of the locking ring 30, the locking ring is free to expand to its original size when it reaches this position.

Once the locking ring 30 reaches the lower region 28 of the plate hole 25, the orthopedic plate 20 becomes locked into place, as translation of the screw 10 is prevented by interference between the locking ring 30 and the shoulder 55. Nonetheless, free screw rotation is allowed should additional tightening be needed to more firmly secure the plate to the bone.

Figure 2B:
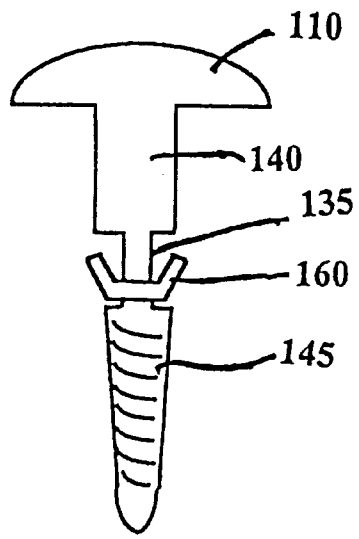
FIG. 2B is side view illustration of the screw and locking combination constructed and operative in accordance with an alternative embodiment of the present invention.
Figure 2C:
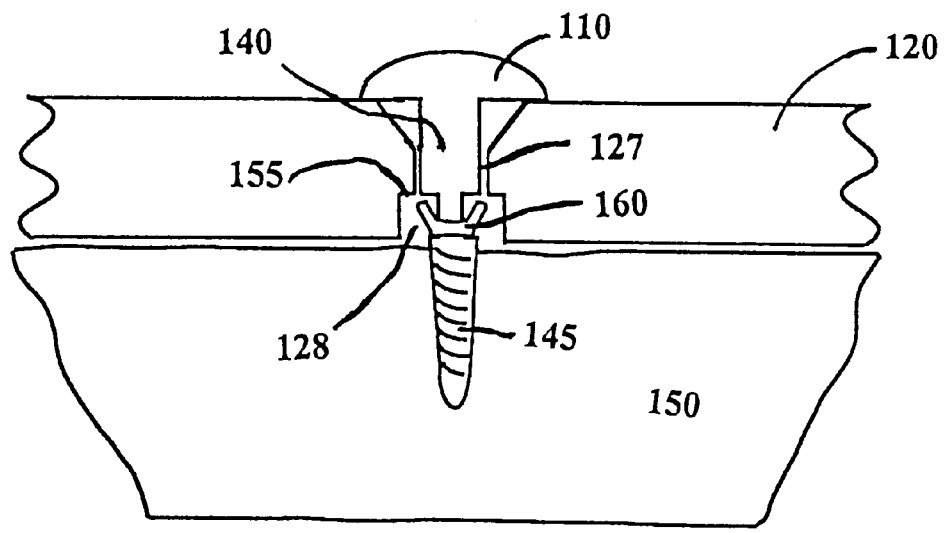
FIG. 2C is a side view illustration of the assembled fixation-assembly constructed and operative in accordance with an alternative embodiment of the present invention.

FIGS. 2A–C illustrate an alternative embodiment of the present invention, in which a crown ring is used as the locking ring. The crown ring 160, shown in FIG. 2A, has two or more tines 165, although only two are shown in the drawing. Like the split ring, the crown ring 160 is preferably made from an elastic material, such as titanium, stainless steel, polymer or a shape memory alloy, but other materials capable of being elastically deformed may also be used.

The crown ring 160 is preferably made as an integral unit with the screw 110, as shown in FIG. 2B. However, it is possible to make the crown ring 160 as a separate unit that is attached to the recessed area 135 of the screw 110. In either case, the inside diameter of the crown ring 160 is larger than the diameter of the recessed area 135 of the screw 110, but is smaller than the diameter of the shank 140 and threaded portion 145. The crown ring 160 is held in the recessed area 135 by the interference between the crown ring 160 and the upper and lower shoulders of the recessed area 135.

The screw 110, plate 120 and plate hole 125 remain essentially unaltered from the preferred embodiment shown in FIGS 1A–1D. The width of the narrow upper region 127 of the plate hole 125 is less than the width of the crown ring 160, while the width of the wide lower region 128 is greater than the width of the crown ring. As with the preferred embodiment, the plate 120 is arranged so that the wide lower region 128 of the plate hole 125 is adjacent to the bone 150, while the narrow upper region 127 is away from the bone.

Once the crown ring 160 is attached to the recessed area 135 of the screw 110, the orthopedic plate 120 is attached to the bone 150 in much the same way as with the preferred embodiment, as shown in FIG. 2C. Because of the relative widths of the crown ring 160 and the narrow upper region 127 of the plate hole 125, the crown ring 160 must be elastically compressed into the recessed area 135 of the screw 110 as the screw 110 and crown ring 160 combination is threaded through the plate hole 125 and into the bone 150. As the screw 110 is threaded further into the bone 150, the crown ring 160 passes through the narrow upper region 127 of the plate hole 125 and reaches the wider lower region 128 of the plate hole 125, where the crown ring 160 is again free to expand to its normal width. In so doing, the plate 120 becomes locked into place on the bone 150, as the screw 110 is prevented from loosening or migrating out of the bone by the interference between the crown ring 160 and the shoulder 155. Nonetheless, free rotation of the screw 110 is allowed should further tightening be needed.

It will be appreciated that with the present invention, removal of the orthopedic plate intact once in place requires advancing all screws incrementally and equally. Using a shape memory alloy makes removal of the screws easier, as only a change in temperature is required to change the shape of the screw to allow it to be loosened. Furthermore, proper alignment prior to fixation is more important than with the prior art. One approach is to use temporary screws made of a soft material for alignment replacing each in turn with the locking version once proper alignment is verified.

The present invention has been described in relation to particular embodiments which are intended in all respects to be illustrative rather than restrictive. Alternative embodiments will become apparent to those skilled in the art to which the present invention pertains without departing from its spirit and scope. Accordingly, the scope of the present invention is defined by the appended claims rather than the foregoing discussion.

What is claimed is:

1. A fixation assembly for fixating an orthopedic plate to a bone, said fixation assembly comprising:

a screw having an upper shank section, a middle section with a recessed area, and a lower threaded section;

a locking ring surrounding the recessed area of said screw, the diameter of said locking ring being greater than the diameter of the recessed area of said screw and less than the diameter of the shank and threaded sections of said screw; and an orthopedic plate having a hole for receiving said screw and said locking ring, the hole including an upper section and a lower section, wherein the width of the upper section is less than the width of said locking ring so that said locking ring is compressed while in the upper section of the hole, and wherein the width of the lower section is greater than the width of said locking ring so that said locking ring is not compressed while in the lower section of the hole.

2. The fixation assembly of claim 1, wherein said locking ring is comprised of an elastic material.

3. The fixation assembly in claim 1, wherein said locking ring is a split ring.

4. The fixation assembly in claim 1, wherein said locking ring is a crown ring.

5. The fixation assembly in claim 4, wherein said crown ring and said screw are an integral unit.

6. The fixation assembly in claim 1, wherein the upper section of the hole in said orthopedic plate is tapered to facilitate compression of said locking ring and threading of said screw.

7. A method of fixating an orthopedic plate to a bone, said orthopedic plate including a hole for receiving a screw and a locking ring, the hole including an upper section and a lower section, wherein the width of the upper section is less than the width of the locking ring so that the locking ring is compressed while in the upper section of the hole, and wherein the width of the lower section is greater than the width of the locking ring so that the locking ring is not compressed while in the lower section of the hole, said method comprising the steps of:

attaching the locking ring to a recessed area of the screw;

inserting the screw into the hole in the orthopedic plate so that the locking ring is compressed into the recessed area of the screw while in the upper section of the hole;

advancing a threaded portion of the screw into the bone until the locking ring reaches the lower section of the hole in the orthopedic plate so that the locking ring returns to its original size and prevents the screw from translating out of the bone.

8. The method of claim 7, wherein said locking ring is comprised of an elastic material.

9. The method of claim 7, wherein said locking ring is a split ring.

10. The method of claim 7, wherein said locking ring is a crown ring.

11. The method of claim 7, wherein the upper section of the hole in the orthopedic plate is tapered to facilitate compression of the locking ring and threading of the screw.

12. The fixation assembly of claim 1, wherein said locking ring is comprised of a shape memory alloy.

13. The method of claim 7, wherein said locking ring is comprised of a shape memory alloy.

* * * * *